(12) United States Patent
Zupp et al.

(10) Patent No.: US 9,200,628 B2
(45) Date of Patent: Dec. 1, 2015

(54) PERISTALTIC PUMP WITH ADJUSTING RING

(75) Inventors: Andre Zupp, Dessau (DE); Uwe Schwerdtfeger, Amesdorf (DE)

(73) Assignee: ULRICH GMBH & CO. KG, Ulm (DE)

( * ) Notice: Subject to any disclaimer, the term of this patent is extended or adjusted under 35 U.S.C. 154(b) by 439 days.

(21) Appl. No.: 13/579,124

(22) PCT Filed: Dec. 23, 2010

(86) PCT No.: PCT/EP2010/070713
§ 371 (c)(1),
(2), (4) Date: Oct. 29, 2012

(87) PCT Pub. No.: WO2011/107178
PCT Pub. Date: Sep. 9, 2011

(65) Prior Publication Data
US 2013/0045122 A1   Feb. 21, 2013

(30) Foreign Application Priority Data

Mar. 1, 2010   (DE) .......................... 10 2010 000 591

(51) Int. Cl.
*F04B 43/08* (2006.01)
*F04B 43/12* (2006.01)
*A61M 5/142* (2006.01)

(52) U.S. Cl.
CPC ........ *F04B 43/1284* (2013.01); *A61M 5/14232* (2013.01); *F04B 43/08* (2013.01); *F04B 43/1253* (2013.01)

(58) Field of Classification Search
CPC ...... F04B 45/08; F04B 43/12; F04B 43/1253; F04B 43/1284; F04B 43/08; F04B 43/0072; F04B 43/123; F04B 43/1238; A61M 39/28; A61M 5/14232; A61B 6/481

USPC ........ 417/477.1, 477.11, 477.9, 477.4, 477.6, 417/477.8, 477.2, 360, 476, 475; 418/70, 418/45, 56, 39
See application file for complete search history.

(56) References Cited

U.S. PATENT DOCUMENTS 3,384,080 A * 5/1968 Muller .......................... 604/153
3,583,838 A * 6/1971 Stauber .......................... 418/45
(Continued)

FOREIGN PATENT DOCUMENTS

AT       367874       8/2007
DE   60123086 T2    6/2007
(Continued)

OTHER PUBLICATIONS

13579124—Proquest translation of FR2157184A5.*
(Continued)

*Primary Examiner* — Devon Kramer
*Assistant Examiner* — Jon Hoffmann
(74) *Attorney, Agent, or Firm* — Fleit Gibbons Gutman Bongini & Bianco PL; Martin Fleit; Paul D. Bianco (57) ABSTRACT

A peristaltic pump squeezes a hose between squeezing rollers and a counter bearing to move fluid through the hose. To compensate for production tolerances and non-uniformities in hose thickness, and to also keep the mechanical loading of the hose as low as possible during the operation of the pump, the spacing between the squeezing rollers and the active surface of the counter bearing can be varied. The counter bearing has a conical or cone-shaped adjusting surface which is supported against a complementarily shaped support surface on the pump housing. The spacing between the squeezing elements and the active surface of the counter bearing can be adjusted by moving the counter bearing relative to the support surface.

20 Claims, 7 Drawing Sheets

(56) References Cited

U.S. PATENT DOCUMENTS

| | | | |
|---|---|---|---|
| 4,174,193 A * | 11/1979 | Sakakibara | F04B 43/1253 417/477.8 |
| 4,178,138 A | 12/1979 | Iles | |
| 4,224,882 A * | 9/1980 | Cruse | 111/120 |
| 4,288,205 A * | 9/1981 | Henk | 417/477.3 |
| 5,387,088 A * | 2/1995 | Knapp et al. | 417/53 |
| 5,657,000 A * | 8/1997 | Ellingboe | F04B 43/1276 128/DIG. 12 |
| 6,685,450 B2 | 2/2004 | Bandis et al. | |
| 6,736,617 B2 * | 5/2004 | Domroese | 417/477.7 |
| 6,852,181 B2 | 2/2005 | Wheeler, Jr. | |
| 6,948,638 B2 * | 9/2005 | Tu | 222/209 |
| 2002/0071776 A1 * | 6/2002 | Bandis et al. | 417/477.6 |
| 2003/0111143 A1 | 6/2003 | Wheeler, Jr. | |
| 2007/0059191 A1 * | 3/2007 | Kreidl et al. | 418/45 |
| 2011/0185758 A1 | 8/2011 | Shimokawa et al. | |
| 2014/0127063 A1 * | 5/2014 | Petersen | F04B 43/1253 417/476 |

FOREIGN PATENT DOCUMENTS

| | | | |
|---|---|---|---|
| EP | 2011541 A2 | 7/2009 | |
| FR | 2157184 | 6/1973 | |
| FR | 2157184 A5 * | 6/1973 | F04B 43/0072 |
| JP | 2003113782 A | 4/2003 | |

OTHER PUBLICATIONS

Translation for International Search report for PCT/EP2010/070713 published Sep. 9, 2011.
Written Opinion of ISA International Preliminary Report on Patentability for PCT/EP2010/070713 dated Mar. 6, 2012.
International Preliminary Report on Patentability published on Sep. 3, 2012 for PCT/EP2010/070713.

* cited by examiner

PERISTALTIC PUMP WITH ADJUSTING RING

FIELD OF THE INVENTION

The invention concerns a peristaltic pump.

BACKGROUND OF THE INVENTION

Such peristaltic pumps are particularly used in the area of medical technology, for example, as infusion pumps or in injection and dialysis devices. A generic peristaltic pump is known, for example, from patent AT 367874. It describes a peristaltic pump with several rollers driven by a central part via a planetary gear, in which the rollers, on at least one hose in which the medium to be conveyed is conducted, roll along its free cross-section while squeezing takes place. The rollers are supported in such a way that they can rotate on a rotating carrier with a large clearance and are in a friction-locking contact with at least one part of their circumference while they lie against the hose with the central part. The rotating movement of the carrier and the rollers causes the squeezed site to move along the hose, wherein the medium conducted in the hose is moved onward in the conveyance direction.

By the alternating squeezing, the hose is exposed to a considerable mechanical loading when the pump is running. Especially with the appearance of slack between the surface of the rollers and the hose surface, massive compression and shear forces appear, which stretch and pull the hose. With a high pressure, the hose can therefore be inflated or even destroyed. In order to largely spare the hose and to keep the adjusting effort during the introduction of the hose into the peristaltic pump as low as possible, a counterpressure body pressing the hose against at least one of the rollers is provided in the peristaltic pump known from AT 367874; it is kept on a base plate so it can be moved with respect to the central part of the peristaltic pump in the radial direction and is pretensioned by means of a spring in the direction of the central part. In this way, it is possible to merely place a new hose during the replacement of a hose and to already ensure a sufficient squeezing by the rollers during the pretensioning of the counterpressure body by means of a spring, so as to guarantee the functionality of the pump. Furthermore, tolerances in the pump arrangement and the hoses are compensated by the elastic counterpressure body.

This arrangement known from the state of the art has proved, however, to be susceptible to disruption because the springs that produce the pretensioning of the counterpressure body can lose their clamping force in the course of time or even break with material fatigue. The replacement of the springs, however, is cumbersome and time-consuming. Furthermore, the distance between the rollers and the counter bearing varies over their circumference, and the result is a low pump pressure.

Proceeding from this, the goal of the invention is to present a peristaltic pump, in which the production tolerances of the pump and the material nonuniformities of the hose are compensated as much as possible and the mechanical loading of the hose during the operation of the pump can be kept as low as possible, wherein, at the same time, as high as possible a pump pressure with a low loading of the hose and a handling of the peristaltic pump with the lowest maintenance possible is to be guaranteed. In particular, the effort to set and adjust the peristaltic pump during or immediately after its production and with regular maintenance is to be reduced.

These goals are attained with the peristaltic pump shown and described herein. Preferred embodiments of this peristaltic pump are also disclosed herein.

SUMMARY OF THE INVENTION

The peristaltic pump in accordance with the invention comprises a housing and several squeezing elements, which are preferably designed as squeezing rollers and press the hose, while squeezing takes place, against the active surface of a counter bearing, so that, in this way, the medium conducted in the hose will move on in the conveying direction. The distance between the squeezing elements and the active surface of the counter bearing is thereby variable. In order to make possible a suitable adjustment of the distance between the squeezing elements and the active surface, which exerts the least possible loading on the hose, the invention provides for the counter bearing to have a conical adjustment surface, which is supported against a complementarily shaped supporting surface on the housing. The distance between the squeezing elements and the active surface of the counter bearing can be adjusted by moving the counter bearing relative to the housing along the supporting surface. By the adjustability of the distance between the squeezing elements and the active surface of the counter bearing, it is possible to compensate production tolerances, which inevitably appear during the production of the pump, and any material tolerances in the hose body. The distance between the squeezing elements and the active surface is thereby adjusted for the first time before the first starting of the peristaltic pump and perhaps later with maintenance operations, in such a way that a minimum pressing of the hose is guaranteed, during which the peristaltic pump is functional and the required operating parameters and working points can be attained. An excess pressing of the hose takes place in any case within the framework of admissible hose tolerances. At the same time, the mechanical loading on the entire pump system is reduced and the power consumption in the working points is largely constant, so that a relatively constant electrical power consumption can be attained. On the whole, the service life of the peristaltic pump itself as well as of the hoses used as consumable material can be prolonged.

In a preferred embodiment of the peristaltic pump in accordance with the invention, provision is made so that the counter bearing is coupled on an adjusting ring, which is conducted on an outside thread on the housing of the peristaltic pump and can be moved by rotation relative to the housing in an axial direction relative to the housing between an upper limiting position and a lower limiting position. A slider ring lies against the adjusting ring; with an axial movement of the adjusting ring relative to the housing, it is also moved in the axial direction. A pressure ring is affixed to the slider ring; it in turn is connected to the counter bearing. Upon rotating the adjusting ring relative to the housing, therefore, the conical adjusting surface of the counter bearing moves on the adjusting surface of the housing and pulls the counter bearing with respect to the housing inwards or outwards, depending on the rotating direction of the adjusting ring. If the adjusting ring is moved in the direction of its lower limiting position, then the counter bearing is pulled into the interior of the housing, and with a reverse rotation direction of the adjusting ring, is moved outwards. The counter bearing and the pressure ring affixed on it are preferably designed as a ring segment. Upon moving the conical adjusting surface of the counter bearing along the supporting surface of the housing, the diameter of the counter bearing designed as the ring segment is changed, wherein the clearance, that is, the distance between the active surface of the counter bearing and the squeezing elements (in particular, of the outer circumferential surface of the squeezing rollers), is changed. By a rotation of the adjusting ring relative to the housing, the clearance can be adjusted to the optimal value. For the adjusting of the clearance, a gauge is expediently used, which is inserted during the adjusting operation between the active surface of the squeezing element (that is, in particular, the outer circumference of the squeezing rollers) and the active surface of the counter bearing.

BRIEF DESCRIPTION OF THE DRAWINGS

The invention is explained in more detail below with the aid of an embodiment example with reference to the accompanying drawings. The drawings show the following:

FIG. 6: detailed view of a transverse sectional view of the peristaltic pump of FIG. 2 in the area of the counter bearing and a squeezing roller opposite the counter bearing, wherein

DETAILED DESCRIPTION OF THE INVENTION

Figure 1:
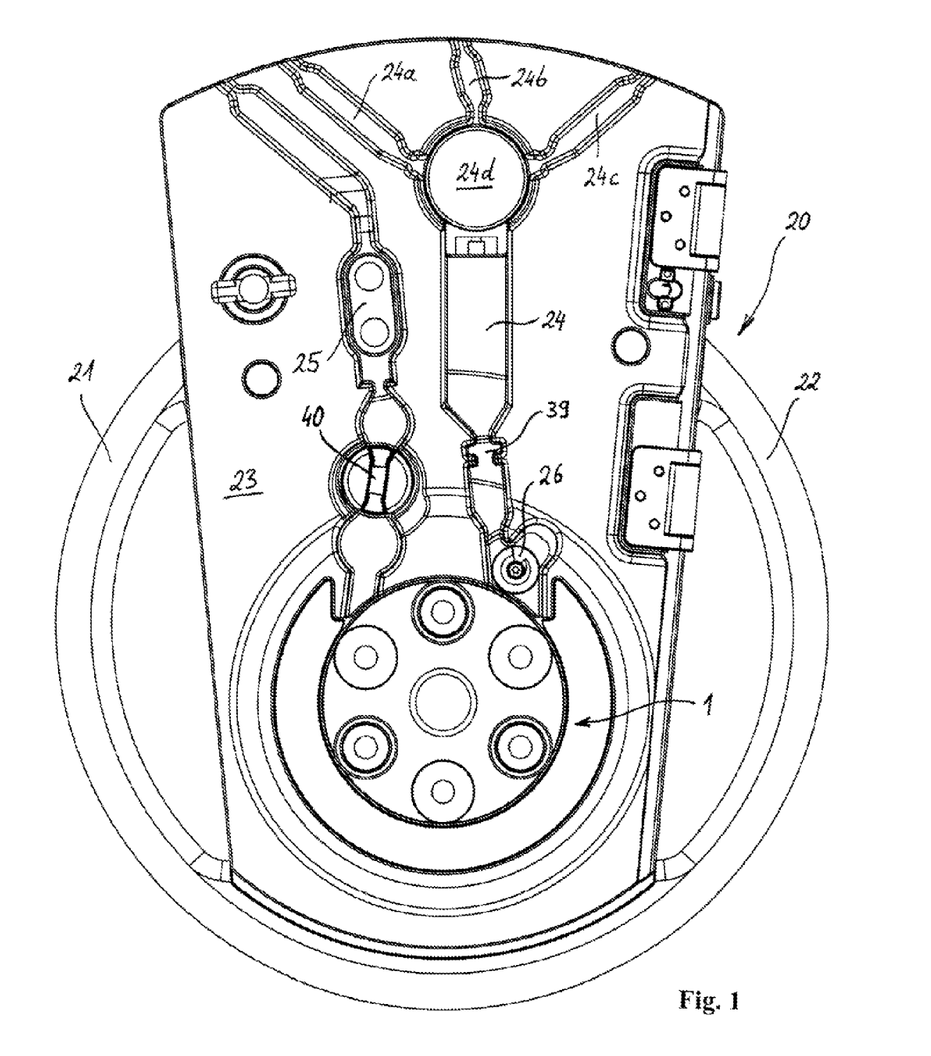
FIG. 1: top view of an injection device in which a peristaltic pump in accordance with the invention is used.

FIG. 1 shows the injection head of an injection device for the injection of two different or similar contrast agents and a NaCl rinsing solution into the bloodstream of a patient, in which a peristaltic pump 1 in accordance with the invention is used. Such injection devices are used, for example, for the injection of contrast agents in the carrying out of imaging methods, such as computed tomography, ultrasound investigations and magnetic resonance tomography (MRT). The injection device comprises the injection head 20, which is shown in FIG. 1 and in which the peristaltic pump 1 is located. The injection head 20 comprises a plastic housing with two circular hand grips 21, 22. A panel 23 is located between the hand grips 21 and 22; it can be closed with a lid that is not depicted here in the drawing. In its lower area, the panel 23 has a recess to hold the peristaltic pump 1. Above it, there are channel-shaped recesses 24, 25, into which the branched hose arrangement (which is not depicted here in the drawing) can be introduced. The hose arrangement is, in particular, a hose arrangement as described in detail in EP 2 011 541 A2. This hose arrangement comprises in total three supply hoses—namely, a first supply hose for a first contrast agent, a second supply hose for a second contrast agent, and a third supply hose for a rinsing solution (in particular NaCl). The three supply hoses are connected to supply flasks for the contrast agents and the rinsing solution, which are also not depicted here in the drawing, and into which branches 24a, 24b, and 24c of the recess 24 located in the upper area of the panel 23 are introduced. The three supply hoses coming from the supply containers are brought together into a hose piece, which is conducted to the peristaltic pump 1 and which is introduced in the circular recess 24d of the panel 23.

To introduce the hose into the peristaltic pump 1, a threading device is provided. The mode of functioning and the design of this threading device will be explained below. The hose is finally conducted through the peristaltic pump 1 and placed in the recess 25 in the upper left part of the panel 23. The end of the hose is connected to a patient hose via which the media conducted in the hose can finally be injected into the bloodstream of the patient. To affix the hose on the panel 23, an affixing device is provided, which makes possible an affixing of the hose to a first entry-side point 39 and at least one second exit-side point 40 of the peristaltic pump. Appropriately, ultrasound sensors for the detection of air bubbles in the hose are located at the affixing sites 39 and 40. Other affixing sites of the hose on the panel 23 are possible and are described, for example, in EP 2011541 A1.

Figure 2:
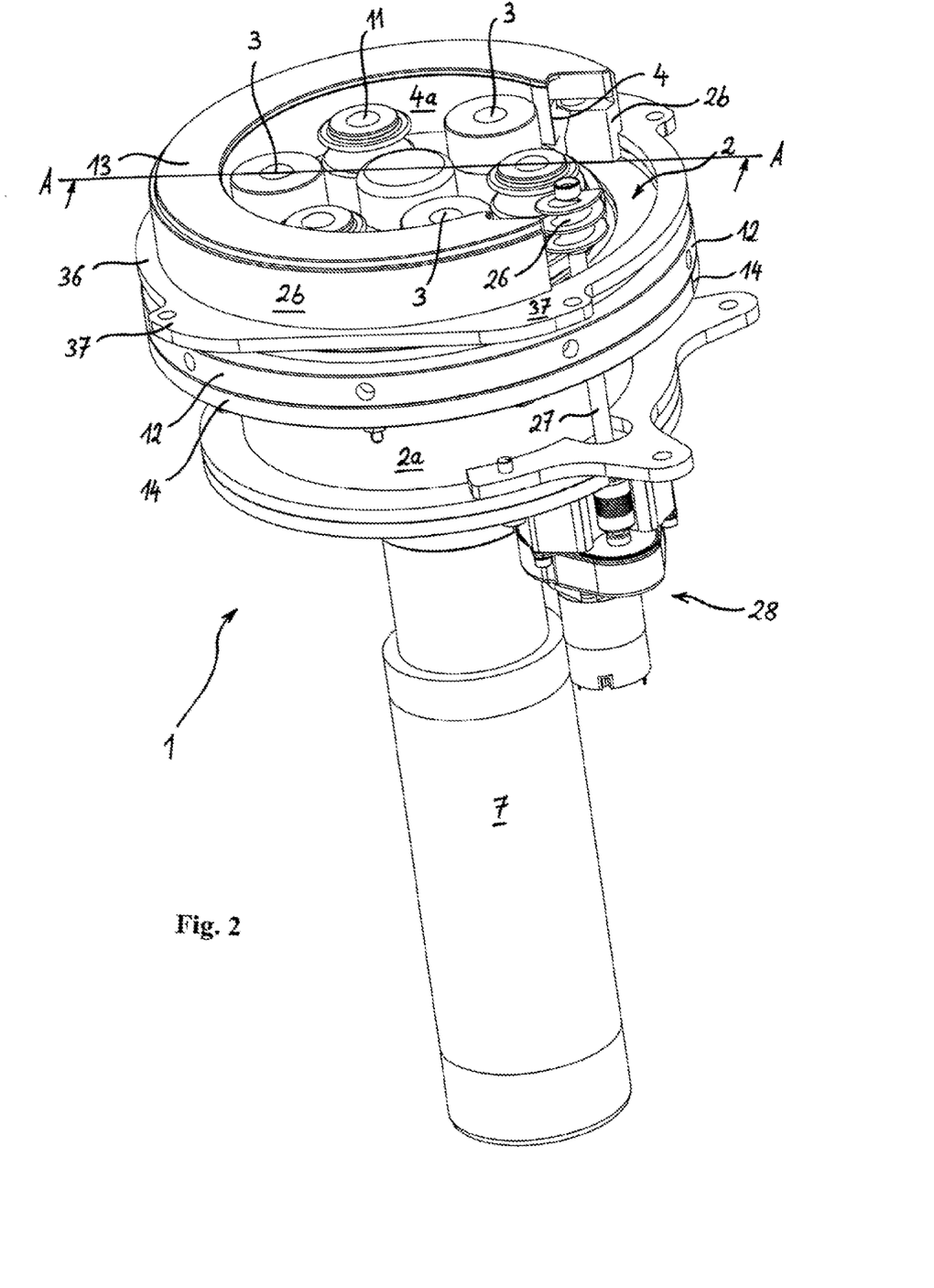
FIG. 2: perspective view of a peristaltic pump in accordance with the invention.
Figure 3:
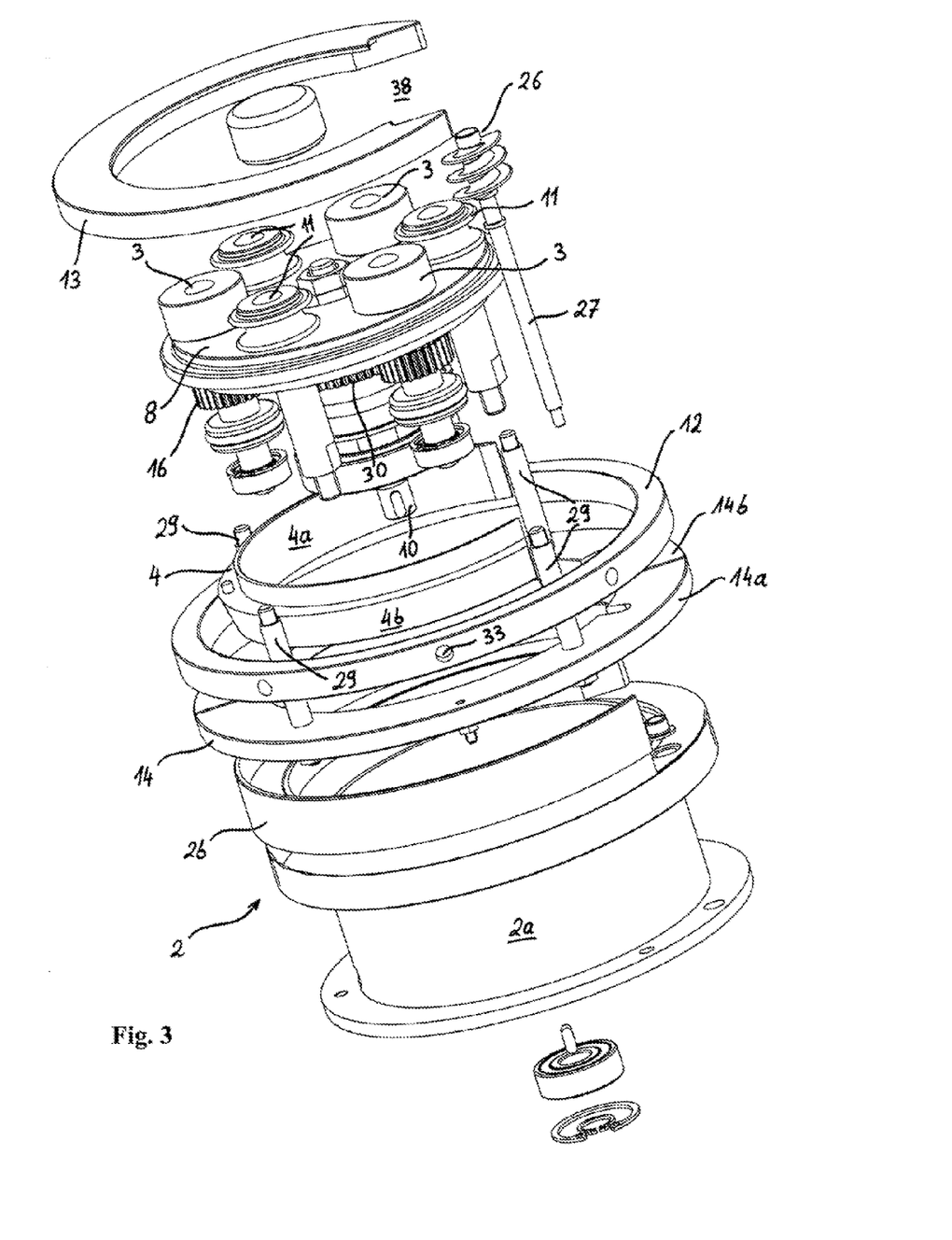
FIG. 3: exploded view of the peristaltic pump of FIG. 2.

FIGS. 2 and 3 show the peristaltic pump 1 in detail in a perspective view, wherein FIG. 3 is an exploded view. The peristaltic pump 1 comprises a lower pump unit with a drive motor 7, and an upper pump unit with a housing 2. The housing 2 is subdivided into a lower housing part 2a and an upper housing part 2b. The lower housing part 2a can be designed with the upper housing part 2b as one part or also in two parts.

Figure 4:
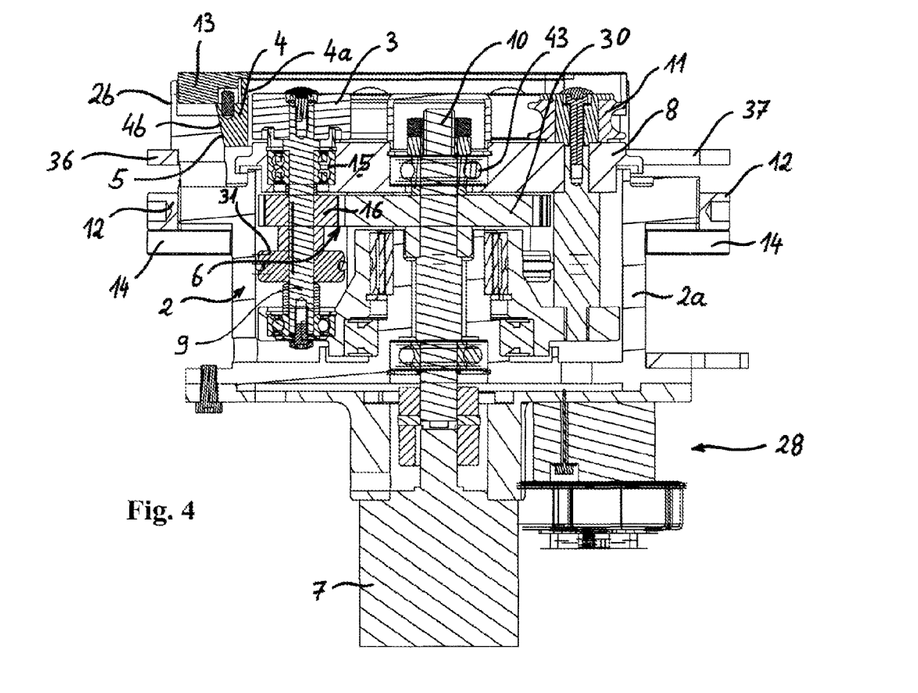
FIG. 4: sectional view of the peristaltic pump of FIG. 2 along the A-A plane.

The lower pump unit comprises the drive motor 7 with a drive shaft 10, which is coupled with the upper pump unit via a gear. The structure of the upper pump unit can be deduced from the sectional view of FIG. 4. A gear 6 coupled with the drive shaft 10 of the drive motor 7 is located in the interior of the housing 2. The gear comprises a sun wheel 30, which is connected in a non-rotatable manner with the drive shaft 10 of the drive motor 7. The upper end of the drive shaft 10 is supported so it can rotate via a first bearing 43 in a carrier disk 8. Several squeezing elements 3 are located on the carrier disk 8. The squeezing elements 3 are driven squeezing rollers 3 in the embodiment example shown in the drawing here, wherein three such squeezing rollers 3 are uniformly located here on the outer circumferences of the circular carrier disk 8. The squeezing rollers 3 are supported on the carrier disk 8 in such a manner that they can rotate. For this, each of the three squeezing rollers 3 is mounted on a shaft 9 with an axis 9' and each shaft 9 is supported via a second bearing 15 in a borehole of the carrier disk 8. The shafts 9 and thus the axes 9' of the squeezing roller 3 run parallel to the drive shaft 10 of the drive motor 7. The drive motor 7 starts the rotation of the carrier disk 8 and the squeezing rollers 3 with a running pump via the gear 6. In addition to the sun wheel 30, the gear 6 comprises planetary wheels 16, wherein such a planetary wheel 16 is correlated with each squeezing roller 3 and is affixed non-rotatably on the shaft 9. Each of the planetary wheels 16 is coupled with the sun wheel 30 of the planetary gear, via teeth. In addition to the planetary wheel 16, a friction wheel 31 is located on each shaft 9, wherein the friction wheel 31 is non-rotatably affixed on the shaft 9 at a distance to the planetary wheel 16. A surrounding groove is located on the outer circumference of each friction wheel 31; a rubber ring 32 (0 ring) is inserted into the groove. Via this rubber ring 32, the friction wheel 31 is in contact with the inner circumference 2c of the pump housing 2. The inner circumference 2c of the housing 2 thus acts as a hollow wheel of a planetary gear. If the drive shaft 10 is made to rotate by the drive motor 7, then this rotation movement is transferred via the coupling of the planetary wheel 16 on the sun wheel 30 to the shaft 9, wherein the shaft 9 and the squeezing roller 3 connected with it in a non-rotatable manner are made to rotate. At the same time, the friction wheel 31 on the inner circumference 2c of the pump housing 2 rolls, wherein the carrier disk 8 is also rotated, relative to the pump housing 2. By means of the friction wheels 31, it is possible also for the drive motor 7 to make the carrier disk 8 rotate if there is still no hose in the peristaltic pump.

Figure 5:
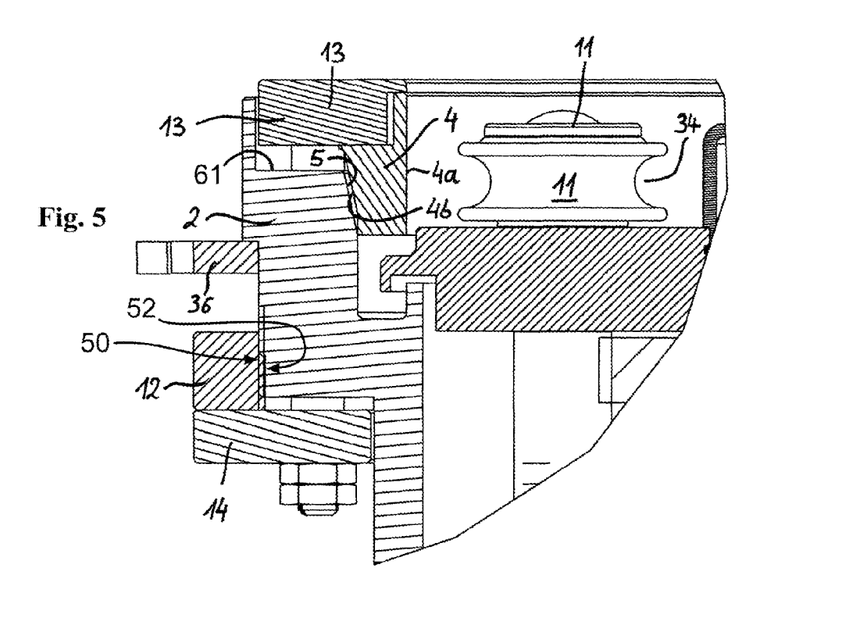
FIG. 5: detailed view of the sectional view of FIG. 4 in the area of the counter bearing and a guide roller opposite the counter bearing.

In addition to the squeezing rollers 3, guide rollers 11 are also supported on the carrier disk 8. The guide rollers 11 are used to guide the hose between adjacent squeezing rollers 3 and are not driven. The guide rollers 11 have a groove 34, which is semicircular in cross-section, on the outer circumference in which the hose is conducted (FIG. 5). The arrangement of the guide rollers 11 and the squeezing rollers 3 on the carrier disk 8 can be deduced, in particular, from the exploded view of FIG. 3.

To introduce the hose into the peristaltic pump, a threading device is provided, which threads the hose automatically between the squeezing rollers 3 and the counter bearing 4. The threading device comprises a screw spindle 26 located outside the carrier disk 8. The screw spindle 26 is located on a shaft 27, wherein the shaft 27 runs parallel to the axis 9' of the squeezing rollers 3. The shaft 27 is supported in a housing part 2 of the peristaltic pump in such a way that it can rotate and is coupled with a spindle drive 28 with which the shaft 27 and the screw spindle 26 can be made to rotate, so as to thread a hose placed in the screw spindle into the peristaltic pump. The upper screw flights of the screw spindle 26 protrude in the longitudinal direction of the peristaltic pump (that is, parallel to the axis of the shafts 10 and 27) via the upper side of the squeezing rollers 3 and the guide rollers 11.

A counter bearing 4 is located on the upper end of the upper pump unit. The counter bearing 4 is designed in the shape of a circular segment with a recess 38 and appropriately extends over an angle range of 200-300°. The screw spindle 26 is located in the area of the recess 38 of the counter bearing 4. The counter bearing 4 has an active surface 4a, which is opposite the outer circumference of the squeezing rollers 3 at a distance d. The hose is threaded into the gap between the active surface 4a and the outer circumference of each squeezing roller 3.

To introduce the hose into the peristaltic pump 1, the hose piece to be introduced is first affixed via the affixing device on the two affixing sites 39 and 40 on the panel 23. The hose piece between the affixing devices 39 and 40 then has (as a result of the bounce of the hose piece) the form of a loop. Subsequently, the hose piece is placed in the screw spindle 26. Then, the pump is started, wherein the drive motor 7 makes the carrier disk 8 rotate. At the same time, the spindle drive 28 makes the screw spindle 26 rotate. For this purpose, the spindle drive 28 is coupled with the control of the drive motor 7. By means of the rotation of the screw spindle 26, the hose is conducted from the screw spindle 26 downwards in the direction of the carrier disk 8. By the rotation of the carrier disk, one of the guide rollers 11 is moved toward the hose and the hose meshes into the groove 34 on the outer circumference of the guide roller 11. By further rotation of the carrier disk 8, the guide roller 11 located on it moves on in the conveyance direction of the pump and thereby pulls the hose by fraction in the groove 34, on the one hand, downwards in the direction of the carrier disk 8 and presses it, on the other hand, in a radial direction outwards against the counter bearing 4. With a further rotation of the carrier disk 8, the guide roller 11 pulls the hose further into the peristaltic pump along the inner circumference of the counter bearing 4 shaped as a circular segment as a result of the static friction on the hose surface and the traction in the groove 34 on its outer circumference, until the carrier disk has carried out (almost) a complete rotation with the guide roller 11 located on it, and the hose is pulled completely into the peristaltic pump by further rotation of the carrier disk. By the rotation of the carrier disk, the hose is finally squeezed against the counter bearing 4 by the squeezing roller 3 following on the carrier disk 8 of the guide roller 11. In this way, the hose is automatically introduced between the outer circumference of the squeezing rollers 3 and the counter bearing 4 and with a further rotation of the carrier disk 8 is squeezed for the conveyance of the liquid conducted therein.

If the hose is completely introduced into the peristaltic pump, then the squeezing rollers 3 press the hose while the peristaltic pump is running (that is, with rotating carrier disk 8 and rotating squeezing rollers 3) and while squeezing the hose diameter against the active surface 4a of the counter bearing 4 in order to further convey in this way the medium conducted in the hose in the conveyance direction (that is, in the rotation direction of the carrier disk 8).

After ending the pumping operation, the threading device can also be used to thread out the worn hose when a replacement of the hose is required. To this end, the spindle drive 28 is operated when the peristaltic pump is running in the reverse rotation direction. In this way, the screw spindle 26 pulls the hose piece placed in the peristaltic pump upwards so that the meshing of the hose in the groove 34 of the guide rollers 11 is loosened. After a complete rotation of the carrier disk, the hose is pulled completely out of the peristaltic pump and can be removed after loosening the affixing elements on the affixing sites 39 and 40 and can be replaced by a new hose. For the introduction of the threading out of a worn hose, a control routine in the control of the spindle drive 28 is provided, which can be triggered with the pressing of a button by the operator.

For the optimal adjustment of the distance between the counter bearing 4 and the squeezing rollers 3, the counter bearing with its active surface 4a, in a preferred embodiment example, is placed on the housing 2 in such a way that it can be moved relative to the squeezing rollers 3. To this end, the counter bearing 4 is connected with a pressure ring 13. The pressure ring 13 is also a ring with the shape of a circular segment. The counter bearing 4 has an adjusting surface 4b opposite the active surface 4a. It is conical or cone-shaped. The arrangement, consisting of the counter bearing 4 and the pressure ring 13, is located in the upper opening of the housing 2 in such a way that the conical adjusting surface 4b of the counter bearing 4 is supported against a complementary supporting surface 5 on the housing 2, which has a complementary shape (that is, it is also conical or cone-shaped), wherein the supporting surface 5 on the housing 2 expands conically downwards (that is, into the interior of the housing) (FIG. 6, each, above and to the left).

On the outside of the housing 2, an affixing ring 36 affixed on the housing (which had to be omitted in FIG. 3 for reasons of clarity) is provided with affixing flanges 37 to affix the housing 2 on the panel 23 of the injection head 20. Moreover, in the transition area between the lower housing part 2a and the upper housing part 2b, an adjusting ring 12 is located on the outside of the housing 2. The adjusting ring 12 is a circular ring, which has an inner thread 50 on the inside surface of the circle. An outside thread 52, which is complementary to this inside thread 50, is provided on the outside of the housing 2. The adjusting ring is coupled with the housing 2 via this thread arrangement in such a manner that by a rotation of the adjusting ring 12 relative to the housing 2, the adjusting ring can be continuously moved in the axial direction between an upper limiting position and a lower limiting position with respect to the housing 2. Several boreholes 33 with which a pin can engage are provided on the outer circumference of the adjusting ring 12 for the rotation of the adjusting ring 12 relative to the housing 2.

A slider ring 14 fits against the underside of the adjusting ring 12. The slider ring 14 is composed of two semi-circular ring segments 14a and 14b and is connected via several bolts 29 with the pressure ring 13 (FIG. 3).

The distance d between the squeezing rollers 3 and the active surface 4a of the counter bearing 4 can be adjusted via the arrangement consisting of the counter bearing 4, the pressure ring 13, the slider ring 14, and the adjusting ring 12.

Figure 6A:
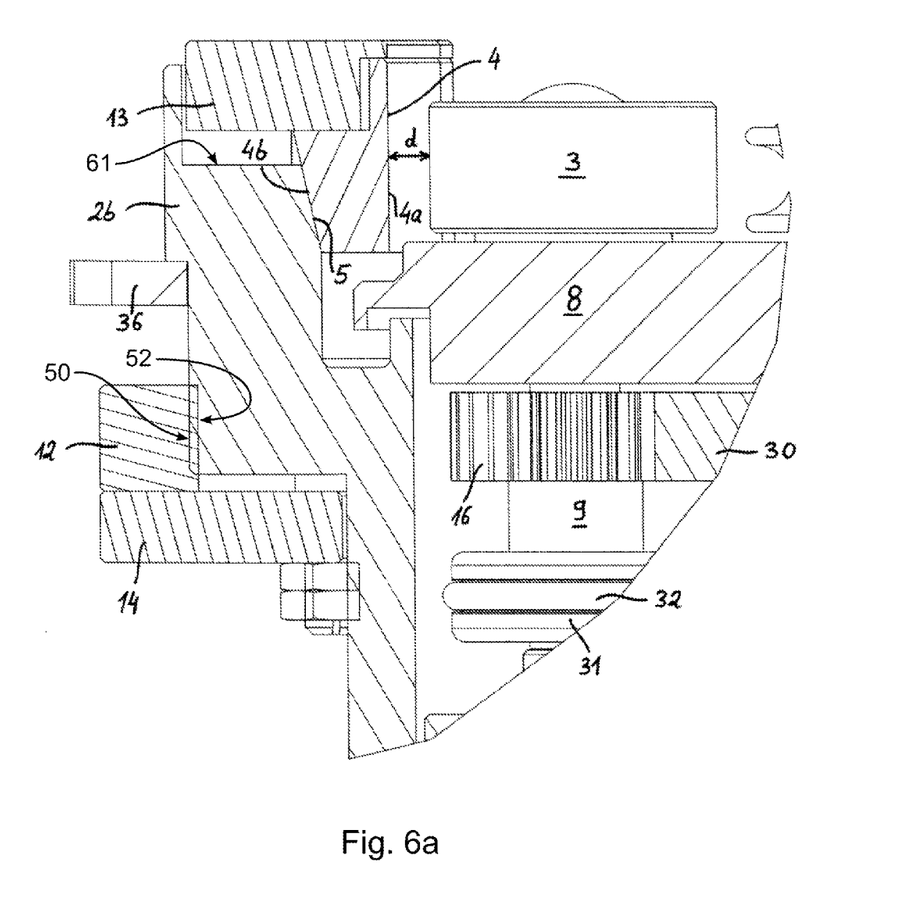
FIG. 6a shows the counter bearing in its first (upper) limiting position and FIG. 6b, the counter bearing in its second (lower) limiting position.
Figure 6B:
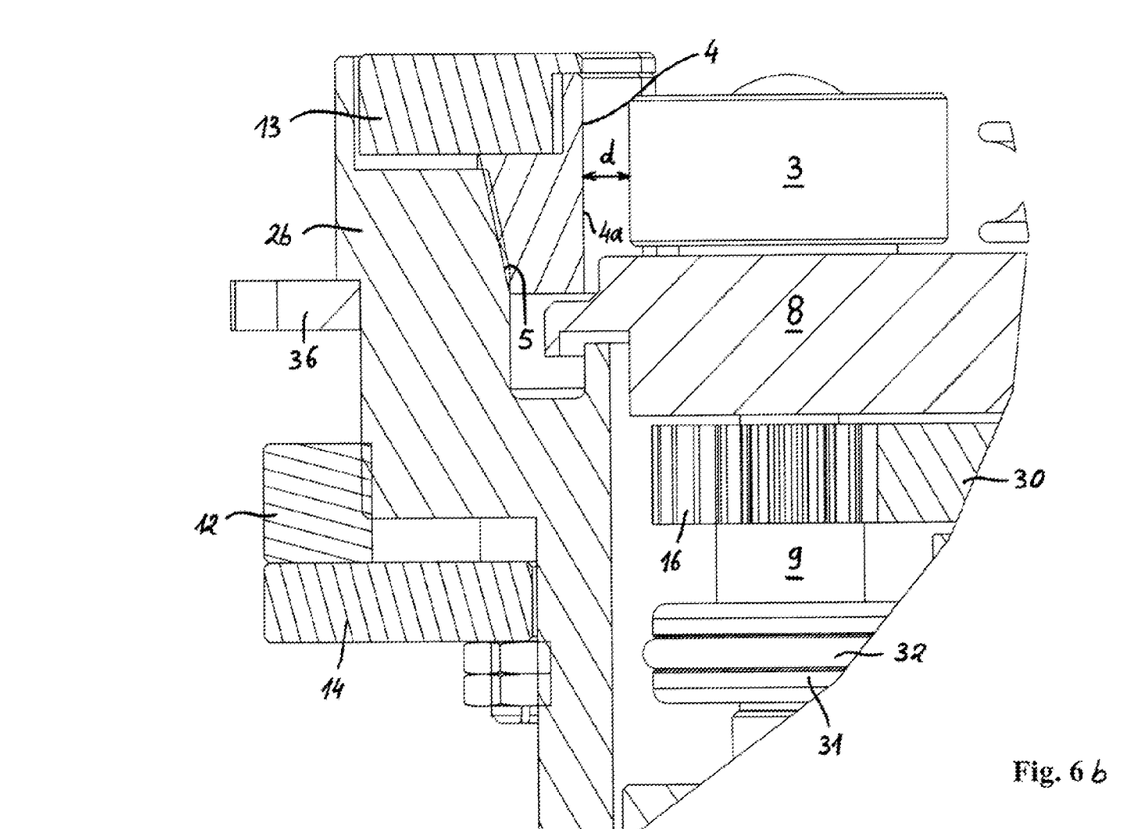
Figure 7:
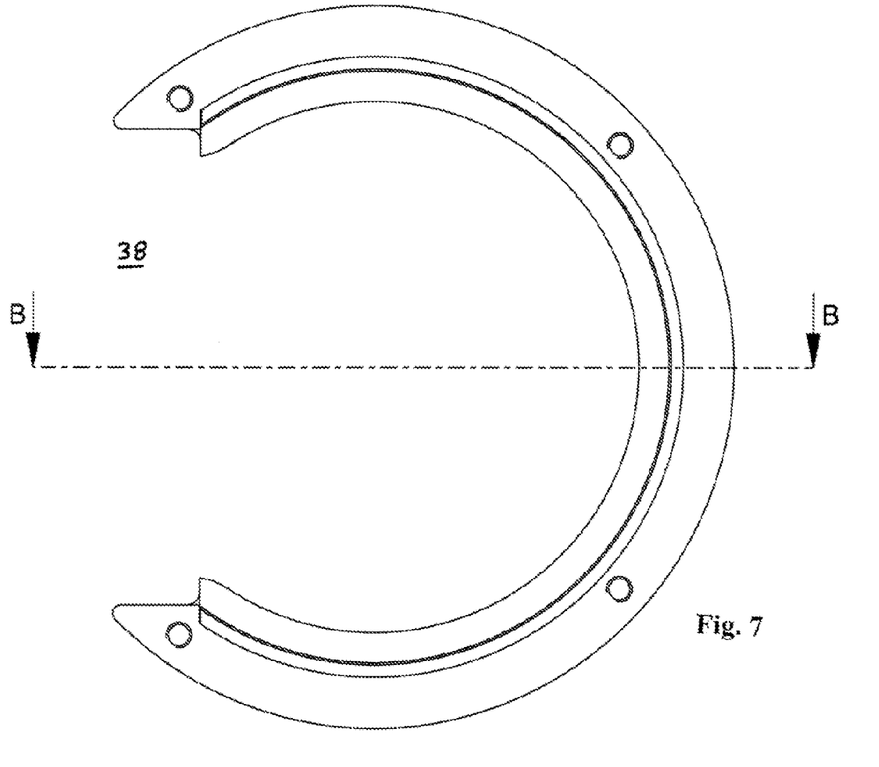
FIG. 7: top view of the counter bearing of the peristaltic pump of FIG. 2 and the pressure ring connected with the counter bearing.
Figure 8:
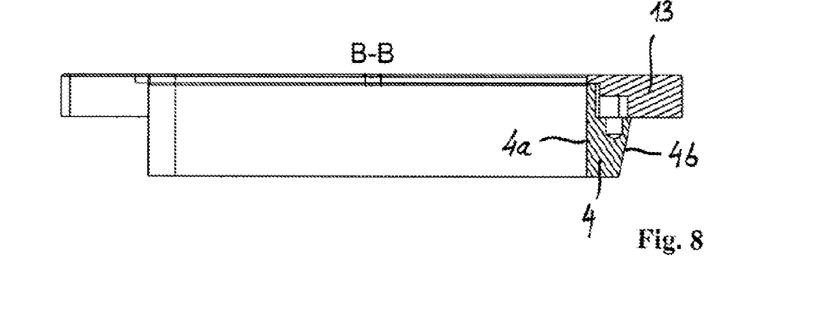
FIG. 8: sectional view of the counter bearing and the pressure ring of FIG. 7, connected with it along the B-B plane.

In order to maximize the distance d between the outer circumference of the squeezing rollers 3 and the active surface 4a, the counter bearing 4 is brought to its first (upper) limiting position (FIG. 6a). Proceeding from here, the distance d can be reduced in that the adjusting ring 12 on the housing 2 is rotated in the direction of its lower limiting position. In this way, the adjusting ring 12 moves from its upper limiting position downwards. Thus, the slider ring 14, which fits against the underside of the adjusting ring 12, is also moved downwards relative to the housing. Since the slider ring 14 is connected with the pressure ring 13 via the bolts 29, the pressure ring 13 with the counter bearing 4 affixed thereon is also moved downwards in this way. The adjusting surface 4b of the counter bearing 4 on the conical supporting surface 5 thereby slides along the housing 2. With this movement, the counter bearing 4 with the shape of a circular segment is readily constricted and reduces its diameter, wherein the active surface 4a is pressed in the radial direction toward the squeezing rollers 3 or the guide rollers 11. By means of this movement, the distance d between the active surface 4a and the outer circumference of the squeezing roller 3 is reduced. If the adjusting ring 12 arrives at its lower limiting position with a further rotation, then the underside of the pressure ring 13 sits on a base 61 of the housing 2. In this position, the distance d between the active surface 4a and the outer circumference of the squeezing roller 3 or the guide rollers 11 is in a minimal position (FIG. 6b).

By this arrangement of the counter bearing 4, the clearance (that is, the distance d) between the active surface 4a and the outer circumference of the squeezing rollers 3 can be adjusted to a value that is optimal for the operation of the pump. This adjustment takes place for the first time before the starting of the peristaltic pump. For the adjustment of a desired distance d, a gauge is appropriately used, whose thickness corresponds to the clearance to be set and which is placed between the active surface 4a and the outer circumference of the squeezing rollers 3. Subsequently, the adjusting ring 12 is rotated relative to the housing until the active surface 4a and the outer circumference of the squeezing roller 3 fit closely against the outer surfaces of the gauge. The clearance can be readjusted if necessary when maintenance is carried out on the peristaltic pump.

The invention is not limited to the described embodiment example. Thus, the invention can be used not only in radial peristaltic pumps but rather, for example, also in peristaltic pumps with a linear mode of action, such as in so-called linear peristaltic pumps or travelling wave pumps. The use of the peristaltic pump in accordance with the invention is furthermore not limited to injection devices, but rather extends also to other pump devices, such as infusion pumps.

The invention claimed is:

1. A peristaltic pump for conveyance of a medium conducted in a hose, comprising a housing with a ramped supporting surface;

a counter bearing forming an open ring and having a ramped adjusting surface mateable with the ramped supporting surface, and an active surface configured to contact the hose during operation of the pump;

a plurality of squeezing elements, the squeezing elements positioned to press the hose against the active surface of the counter bearing when the hose is positioned in the pump, to thereby force the medium to flow in the hose in a conveyance direction, the distance between the squeezing elements and the active surface of the counter bearing being adjustable by moving the counter bearing relative to the supporting surface to thereby slide the ramped adjusting surface against the ramped supporting surface to thereby change a diameter of the counter bearing.

2. The peristaltic pump according to claim 1, wherein the squeezing elements are formed by squeezing rollers which are rotated by a drive motor via a gear.

3. The peristaltic pump according to claim 2, wherein the squeezing rollers are supported on a carrier disk and an axle of each squeezing roller runs parallel to a drive shaft of the drive motor.

4. The peristaltic pump according to claim 3, wherein a guide roller is located on the carrier disk between two adjacent squeezing rollers.

5. The peristaltic pump according to claim 1, wherein the counter bearing is coupled with an adjusting ring which is located on the housing and is movable in an axial direction relative to the housing between an upper limiting position and a lower limiting position.

6. The peristaltic pump according to claim 5, wherein the adjusting ring is engaged with the housing via a thread and by rotation of the adjusting ring relative to the housing, the adjusting ring is movable continuously in the axial direction between the upper limiting position and the lower limiting position.

7. The peristaltic pump according to claim 5, wherein the counter bearing is connected with a pressure ring affixed on a slider ring which fits against the adjusting ring.

8. The peristaltic pump according to claim 7, wherein the slider ring is moving in the axial direction relative to the housing when the adjusting ring is moved or rotated relative to the housing, and the adjusting surface of the counter bearing is thereby moved on the supporting surface of the housing.

9. The peristaltic pump according to claim 8, wherein the adjusting surface of the counter bearing on the supporting surface of the housing is continuously movable between a first limiting position and a second limiting position, wherein the first limiting position corresponds to the upper limiting position of the adjusting ring and the second limiting position corresponds to the lower limiting position of the adjusting ring.

10. The peristaltic pump according to claim 9, wherein the squeezing elements are formed by squeezing rollers having a rolling circumference and the distance between the rolling circumference of the squeezing rollers and the active surface of the counter bearing has a maximum value in the first limiting position of the adjusting surface and a minimum value in the second limiting position of the adjusting surface.

11. The peristaltic pump according to claim 7, wherein the slider ring is formed by two or more ring segments.

12. The peristaltic pump according to claim 1, wherein the distance between the squeezing elements and the active surface is adjustable by moving the counter bearing relative to the housing along the supporting surface.

13. The peristaltic pump according to claim 1, wherein the open ring of the counter bearing forms a ring segment which extends over an angle range of 200-300°.

14. A peristaltic pump for conveying a medium conducted in a hose, the pump comprising:
- a housing with a ramped supporting surface;
- a counter bearing forming a ring segment and having a conical or cone-shaped adjusting surface, and an active surface configured to contact the hose during operation of the pump, wherein the conical or cone-shaped adjusting surface is slidably mateable with the ramped supporting surface of the housing, and the counter bearing is moveable relative to the housing along the supporting surface continuously between a first limiting position and a second limiting position;
- a plurality of squeezing elements configured to press the hose against the active surface of the counter bearing and to thereby force a medium to flow in the hose in a conveyance direction,
- the distance between the squeezing elements and the active surface of the counter bearing being continuously adjustable by moving the counter bearing relative to the housing to thereby slide the conical or cone-shaped adjusting surface along the ramped supporting surface of the housing.

15. The peristaltic pump according to claim 14, wherein the counter bearing ring segment has a changeable diameter, and the diameter of the counter bearing is reduced when the counter bearing is moving from the first limiting position to the second limiting position.

16. The pump of claim 1, further including:
- an adjusting ring threadably connected to the housing and rotatable to be movable relative to the housing;
- a slider ring slidably contacted by the adjusting ring to be movable with respect to the housing when the adjusting ring is rotated;
- one or more shafts connected to the slider ring to be movable as the slider ring is moved;
- a pressure ring connected to the one or more shafts, the pressure ring movable when the one or more shafts are moved, the pressure ring disposed in contact with the counter bearing to move the counter bearing to thereby cause the counter bearing to be adjustable by moving the counter bearing relative to the supporting surface.

17. The pump of claim 1, wherein when the adjusting ring is rotated, the adjusting ring, slider ring, one or more shafts, and pressure ring are moved axially with respect to the housing.

18. A peristaltic pump for conveyance of a medium conducted in a hose, comprising
- a housing with a ramped supporting surface;
- a counter bearing forming an open ring and having a ramped adjusting surface mateable with the ramped supporting surface, and an active surface configured to contact the hose during operation of the pump;
- a plurality of squeezing elements, the squeezing elements positioned to press the hose against the active surface of the counter bearing when the hose is positioned in the pump, to thereby force the medium to flow in the hose in a conveyance direction,
- the distance between the squeezing elements and the active surface of the counter bearing being adjustable by moving the counter bearing axially to thereby slide the ramped adjusting surface against the ramped supporting surface to thereby change a diameter of the counter bearing.

19. The pump of claim 18, wherein the adjusting ring is threadably connected to the housing to be movable continuously in the axial direction between an upper limiting position and a lower limiting position.

20. The pump of claim 18, further including an adjusting ring and a pressure plate, the adjusting ring connected to the pressure plate, the adjusting ring threadably mated to the housing and rotatable with respect to the housing to cause the pressure plate to press against the counter bearing to move the counter bearing axially when the adjusting ring is rotated.

* * * * *